United States Patent [19]

De Blasiis et al.

[11] 4,103,553

[45] Aug. 1, 1978

[54] APPARATUS FOR THE INDIRECT MONITORING OF THE RADIOACTIVE CONTAMINATION OF SURFACES

[75] Inventors: Mario De Blasiis; Antonio Moccaldi; Attilio Rori; Silvano Tagliati, all of Rome, Italy

[73] Assignee: Comitato Nazionale per l'Energia Nucleare-CNEN, Rome, Italy

[21] Appl. No.: 709,185

[22] Filed: Jul. 27, 1976

[30] Foreign Application Priority Data

Sep. 4, 1975 [IT] Italy ................... 51197 A/75

[51] Int. Cl.[2] .................................. G01N 1/04
[52] U.S. Cl. .............................. 73/425; 15/104 R
[58] Field of Search ............... 73/421 R, 421 A, 425; 15/344, 359, 104 R

[56] References Cited

U.S. PATENT DOCUMENTS

| 1,797,557 | 3/1931 | Stine | 15/344 |
|---|---|---|---|
| 3,091,967 | 6/1963 | Hurdlow | 73/421 R |
| 3,554,039 | 1/1971 | Braun | 73/425 |

*Primary Examiner*—Herbert Goldstein
*Assistant Examiner*—Denis E. Corr

*Attorney, Agent, or Firm*—Stevens, Davis, Miller & Mosher

[57] ABSTRACT

A hollow disk is carried on a wheeled frame or trolley which is moved over the surface being examined. The hollow disk is slidable perpendicularly to its surface within certain limits. The disk is double walled and a certain degree of vacuum is maintained in the space between the walls during the apparatus operation.

The disk wall facing the surface being examined is provided with holes and on the outer surface of the same wall a disk of para rubber is spread which is provided with the same array of holes as the hollow disk wall; the holes of the disk wall being aligned with the holes of the para rubber disk.

For each sampling operation a fresh smear disk is applied on the para rubber layer which adheres thereon by the action of the dynamic vacuum existing within the hollow disk. The hollow disk is biased outwards of the frame by a calibrated spring inserted between the disk and the frame structure. The presence of the spring makes the force exerted by the smear disk on the surface being examined independent of the wheeled frame weight. Said force depends only on the spring characteristics.

9 Claims, 9 Drawing Figures

APPARATUS FOR THE INDIRECT MONITORING OF THE RADIOACTIVE CONTAMINATION OF SURFACES

The indirect methods for monitoring the radioactive contamination of surfaces rely upon measuring the amount of radioactivity removed from a surface by applying a dry filter paper on the suspected surface and moving it to rub an area of said surface which is usually about 100 cm². Subsequently the amount of activity is measured which has been collected by the paper as a consequence of the rubbing. Such operation is repeated until the whole suspected area has been smeared. By applying a removal factor the approximate amount of loose radioactive contamination on the suspected surface can be estimated.

The removal factor is affected by various factors such as the pressure applied to the smear, the type of surface to be smeared, the kind of the smearing material and the physical form of the contaminant.

Devices to ensure uniformity of the pressures applied and area sampled in each operation have been already disclosed. Such devices usually rely upon some forms of spring by which a pad is loaded which carries the filter paper smear. The devices of this kind up to now developed are not satisfactory. Their major defects are a scarce uniformity of the sampling operations and a great waste of labour; particular safety measures are also required.

Specifically, when the radioactivity is removed by hand from the contaminated surface, the operator cannot readily adequate the pressure on the paper disk to the roughness of the surface, that is to the friction between the paper and the surface. As a consequence, a rupture of the paper or a tearing of the operator's protective gloves are liable to occur.

The apparatus of this invention is intended for overcoming said drawbacks.

In fact by the use of it the inaccuracy of the current method is greatly reduced in determining the percentage of the removed activity (that is the removal factor).

Furthermore, the apparatus of the invention, thanks to its compactness and easy operation is remarkably advantageous over the prior art devices in routine use by operators in the field of health physics.

The apparatus of this invention comprises mainly a hollow disk carried on a wheeled frame or trolley which is moved over the surface being examined. The hollow disk is slidable perpendicularly to its surface within certain limits. The disk is double walled and a certain degree of vacuum is maintained in the space between the walls during the apparatus operation.

The disk wall facing the surface being examined is provided with holes and on the outer surface of the same wall a disk of para rubber is spread which is provided with the same array of holes as the hollow disk wall, the holes of the disk wall being aligned with the holes of the para rubber disk.

For each sampling operation a fresh smear disk is applied on the para rubber layer which adheres thereon by the action of the dynamic vacuum existing within the hollow disk.

The hollow disk is biased outwards of the frame by a calibrated spring inserted between the disk and the frame structure.

The presence of the spring makes the force exerted by the smear disk on the surface being examined independent of the wheeled frame weights; said force depends only on the spring characteristics and because the hollow disk can travel only a short distance perpendicularly to its plane, that is because the spring undergoes only small depressions during the apparatus operation, said force can be considered constant.

The apparatus comprises a managing bar wherein an exhauster and the related supply battery are incorporated. The bar is connected to the wheeled frame by means of a swivel joint whereby ample changes are permitted of the angle of divergence of the handle with respect to the hollow disk plane. The handle section between the wheeled frame and the exhauster is hollow for communicating the suction by the exhauster to the hollow disk.

The apparatus is also provided with an odometer for measuring the distance traveled over the surface being examined.

The invention will be better understood from the following description and attached drawing of preferred embodiments thereof.

Figure 2:
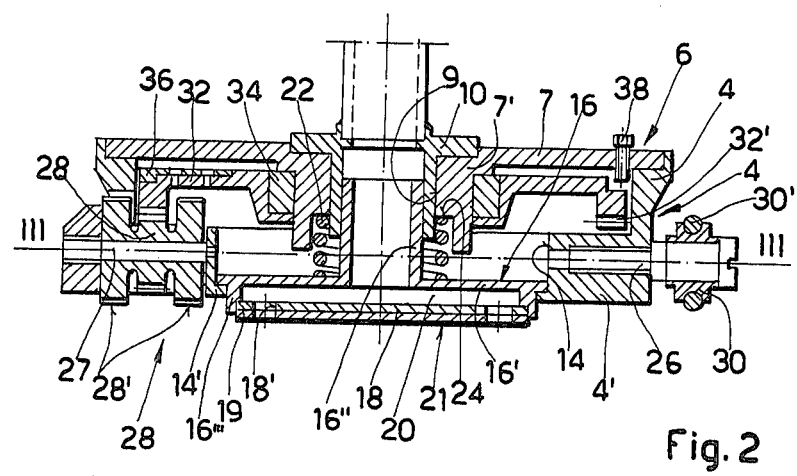
FIG. 2 is a vertical cross section along plane II—II of FIG. 1 of the wheeled frame and related smear carrying disk of the invention.
Figure 1:
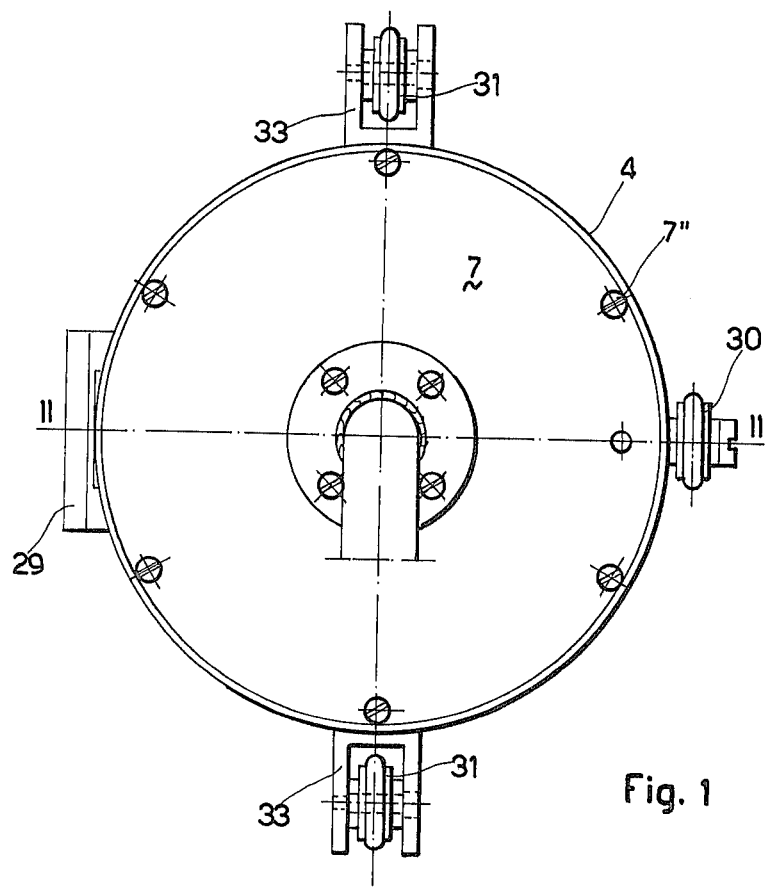
FIG. 1 is a top plan view of the wheeled frame of the apparatus of this invention according to a first embodiment thereof.

Referring now to the drawing and provided that the words "top" and "bottom" are referred to the apparatus as shown in FIG. 2, the apparatus of the invention comprises mainly a wheeled frame 6 of flat cylindrical form to the top surface of which a first section 8 of a pipe is connected in a direction perpendicular to said surface, which pipe at a short distance from the frame is bent at an angle of about 60° with respect to the vertical axis of frame 6.

Figure 5:
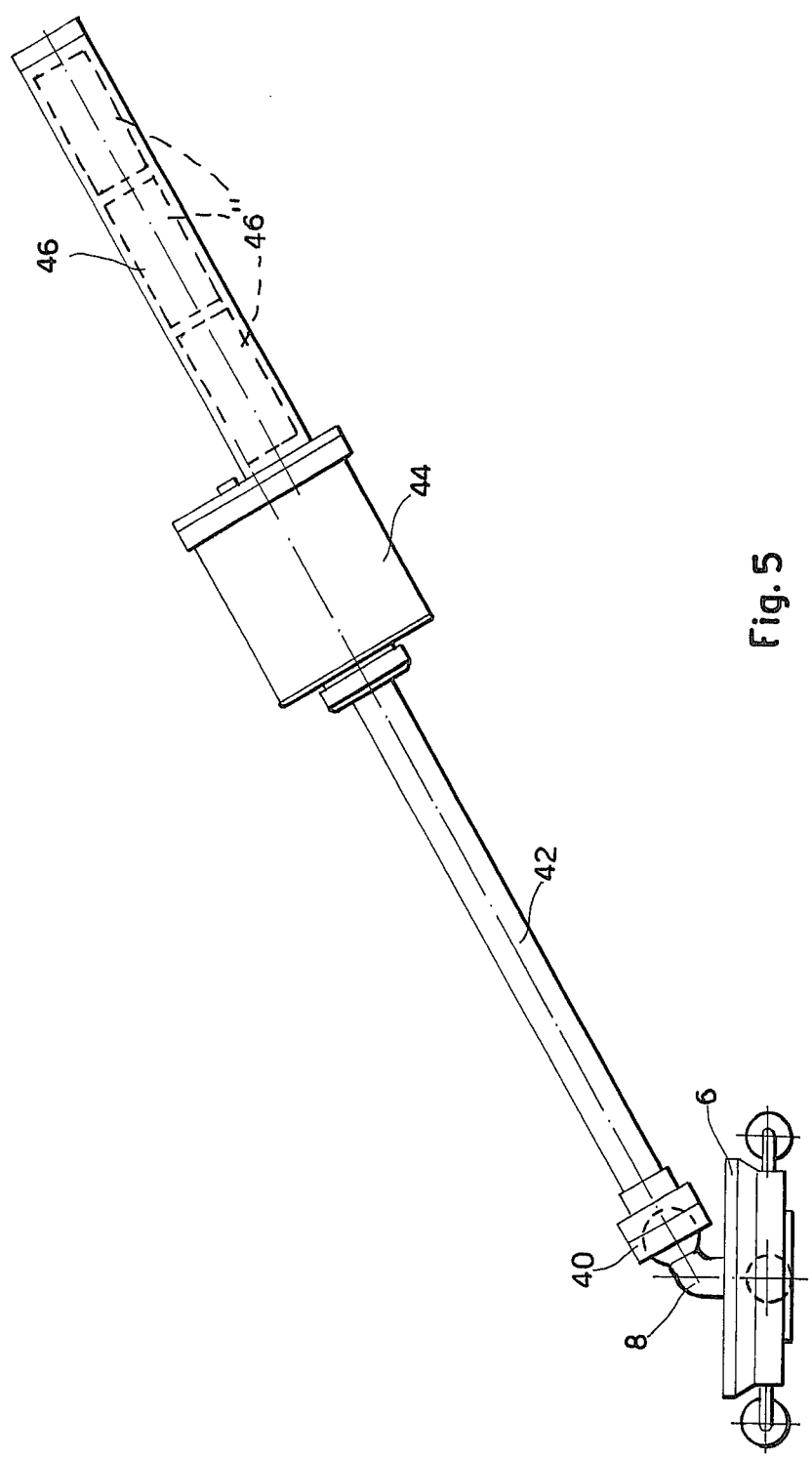
FIG. 5 is a side elevation view of the apparatus of the invention.

At a short distance from the tube bending, in the direction opposite to the wheeled frame, there is provided a joint 40 (FIG. 5) for connecting the first tube section to a second tube 42 which leads to an exhauster 44. At the opposite end of exhauster 44 a handle 46 is attached for managing the apparatus. Wheeled frame 6 comprises a substantially cylindrical housing 4 made of a vertical annular wall 4" and a thick bottom 4'. Housing 4 has a top wall 7 which is fastened to wall 4" by means of screws 7". Top wall 7 is provided with a central hub 7' that is with a hollow downwardly extending cylindrical projection. Into the bore 9 of hub 7' a bushing 10 is received which is fastened to wall 7 by means not shown.

The housing bottom wall is provided with a large bore 14 coaxial with the housing and having an inwardly projecting lip 14' at the lower end of the bore. The vertical wall of bore 14 functions as a guide for a double walled disk 16 slidably fitted therethrough for vertical movement. Lip 14' of bore 14 forms a shoulder for the peripheral projecting lip of disk 16. The upper wall 16' of disk 16 is provided with an upwardly extending stub pipe 16" coaxial with the disk which pipe communicates with the space between the top and bottom walls of the hollow disk and is slidably fitted into said bushing 10. The bottom wall of disk 16 comprises a flat circular plate 18 provided with an array of through holes 18, the edge of the plate being force fitted into a downwardly projecting peripheral rim 16''' of said upper wall 16', a space 20 being defined within disk 16 by said upper wall, plate and rim.

A peripheral projection of rim 16''' extends downwardly beyond the lower surface of plate 18 so as to provide a shallow circular recess wherein a para rubber disk 19 is received which however projects for about one half of its thickness from the same recess.

Disk 19 has the same size as plate 18 and is provided with the same array of through holes. Over disk 19 the smear disk 21 is applied which adheres to the lower surface of disk 19 due to the dynamic vacuum existing within space 20 and due to the friction between the para rubber of which disk 19 is made and the filter paper of which disk 21 is made. Disk 16 can slide vertically being guided by vertical wall of bore 14 while being biased downwardly by a coil spring 22. This is inserted between disk 16 and a circular shoulder 24 of central hub 7' of the housing top wall 7.

Two horizontal axles 26, 27 are firmly attached to lower wall 4' of housing 4 which axles extend outwardly in opposite directions along an axis perpendicular to the vertical symmetry plane of housing 4. On axle 26 a wheel 30 is rotatably mounted which is provided with an elastic tread 30'. On axle 27 a twin wheel 28 is mounted which consists of two similar wheels 28' also with elastic tread. Between the twinned wheels a pinion 28" is fastened thereto which pinion is adapted for cooperating with the teeth 32' of a horizontal crown wheel 32 which is mounted on the central hub 7' of upper wall 7.

A bearing 34 of antifriction metal is inserted between wheel 32 and hub 7'. The upper surface of wheel 32 is provided with a stop plate 36 adapted for engaging a stop pin 38 which projects downwardly from top wall 7. Such device serves for limiting to a predetermined value the amount of area being examined. Plate 36 will have such peripheral extent that, taking into account the gear ratio of pinion 28" and crown wheel 32' and the diameters of twinned wheels 28', the latter will travel a distance corresponding to the surface to be examined before plate 36 abuts against pin 38.

Figure 3:
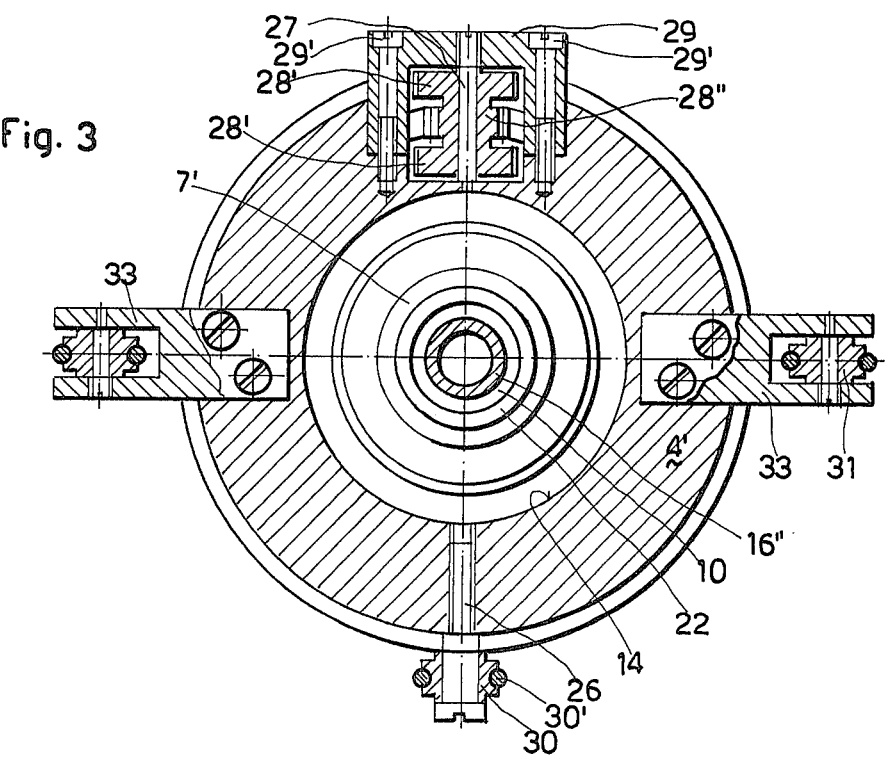
FIG. 3 is a horizontal cross section along line III—III of FIG. 2 of the wheeled frame of the apparatus of this invention.
Figure 4:
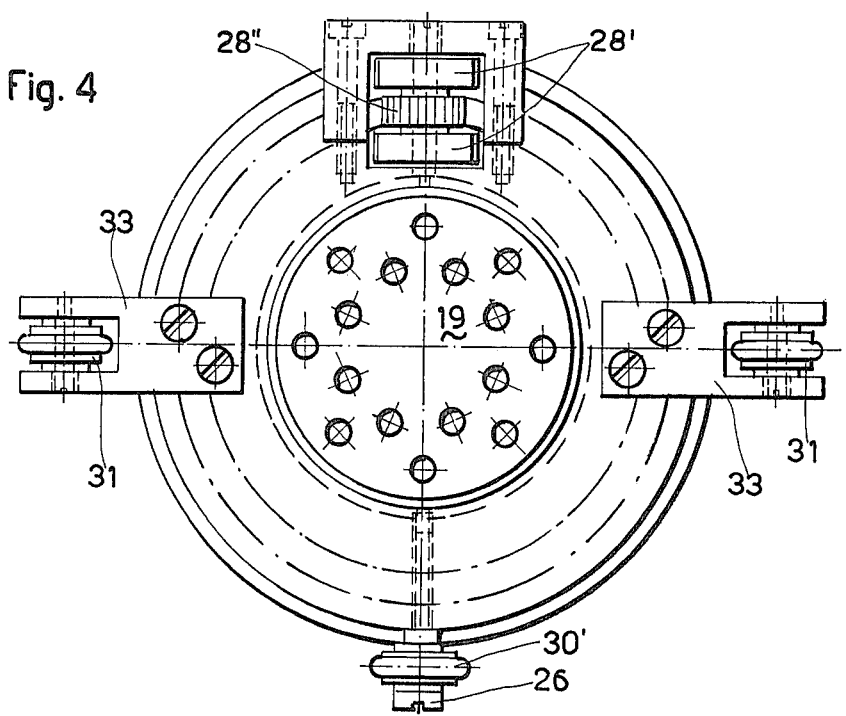
FIG. 4 is a bottom plan view of the wheeled frame of the apparatus of this invention according to the first embodiment thereof.

As shown by FIGS. 3 and 4, a bracket 29 which is fastened to bottom wall 4' of housing 4 by means of two screws 29', is provided which concurs with axle 27 for supporting wheel 28.

Housing 4 is provided with two additional wheels contained in the vertical symmetry plane of frame 6 that is on a plane perpendicular to the wheels already described. Wheels 31 are similar to wheel 30 and are supported each by a fork bracket 33 attached to the lower surface of bottom wall 4' of housing 4.

At the upper end of bushing 10 a first section 8 of a pipe is connected which pipe at a short distance from said bushing is bent to form an angle of about 30° with respect to the plane of top wall 7, that is an angle of about 60° with respect to the vertical.

The first pipe section 8 at its end opposite to bushing 10 is connected with a second straight pipe section 42 by means of a ball joint 40 with adjustable swivel friction. Joint 40 permits an angular displacement of about 15° upwards and about 5° downwards.

Second pipe section 42 connects at the other end with the casing of an exhauster 44.

At the other end of the exhauster casing a handle 46 is provided for managing the apparatus. The batteries 46" for feeding the apparatus are stored within handle 46.

OPERATION

The exhauster 44 is started and a filter paper smear is applied over the lower surface of the pierced para rubber disk 19.

The starting position is then checked of pin 38 which should be in abutment with stop plate 36.

The apparatus is placed on the surface to be examined and driven along a straight path until pin 38 hits the side of the plate opposite to the starting position. The exhauster is then switched off and smear disk 21 is removed from para rubber disk 19 and taken to the analysis laboratory.

Figure 6:
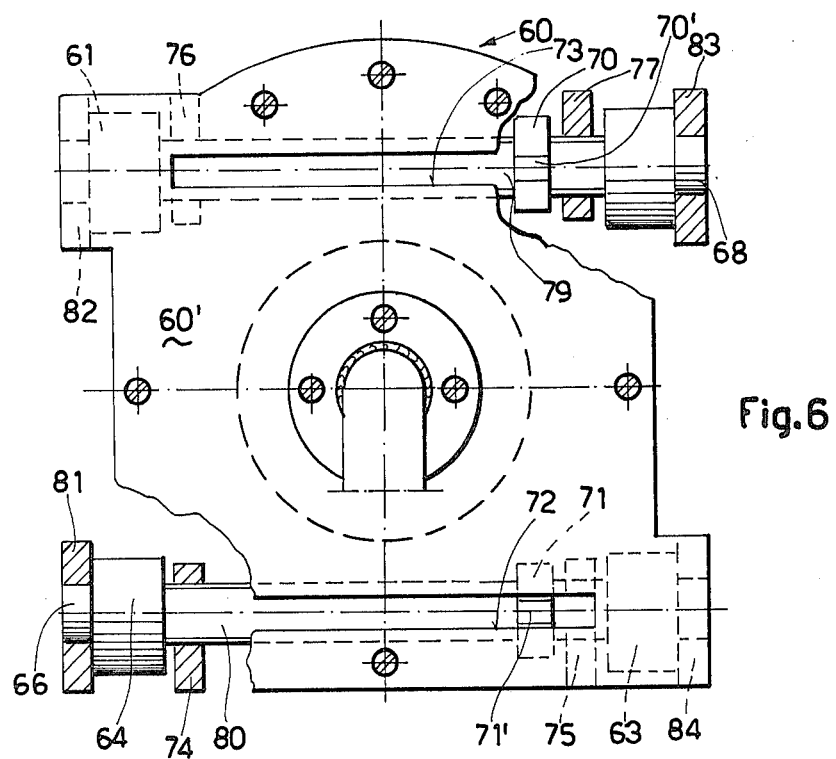
FIG. 6 is a top plan view with parts removed of the wheeled frame of the apparatus of this invention according to a second embodiment thereof.

According to a second embodiment of the invention illustrated by FIG. 6, the wheeled frame 6 is provided with four wheels 61, 62, 63, 64 which are mounted in pairs on two parallel axles 66, 68 perpendicular to the vertical symmetry plane of frame 60 which axles are journalled in bearings 81, 82, 83, 84 attached to the frame. According to this embodiment, axles 66, 68 on which wheels 63, 64 and 61, 62 are respectively mounted are provided with a threading along the sections thereof extending from one wheel to the other of the same axle. Said threading engages a complementarly threaded nut 70, 71 which is provided with transverse projection 70', 71' slidably received in a slot 72, 73 which is provided through the top wall 60' of housing 60. Under wall 60' suitable stops 74, 75, 76, 77 are provided for limiting the travel of nut 70, 71.

The operation of the second embodiment of the invention is as follows:

Wheels 61, 62, 63, 64, when running over the surface to be examined rotate axles 79 and 80 whereby said projections of nuts 70 and 71 are driven along slots 72 and 73 respectively. By setting stops 74, 75, 76 and 77 the travel of nuts 70, 71 and hence the travel of wheeled frame 60 can be limited to a predetermined value. The means for adjusting stops 74, 75, 76, 77 are not shown but are readily envisaged. They may comprise screws to be driven into said nuts through wall 60' in different positions.

Figure 7:
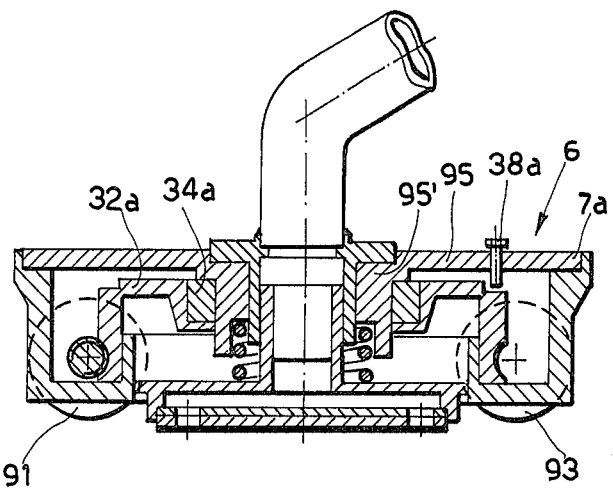
FIG. 7 is a vertical cross section along line VII—VII of FIG. 7a of the apparatus of this invention according to a third embodiment thereof.
Figure 7A:
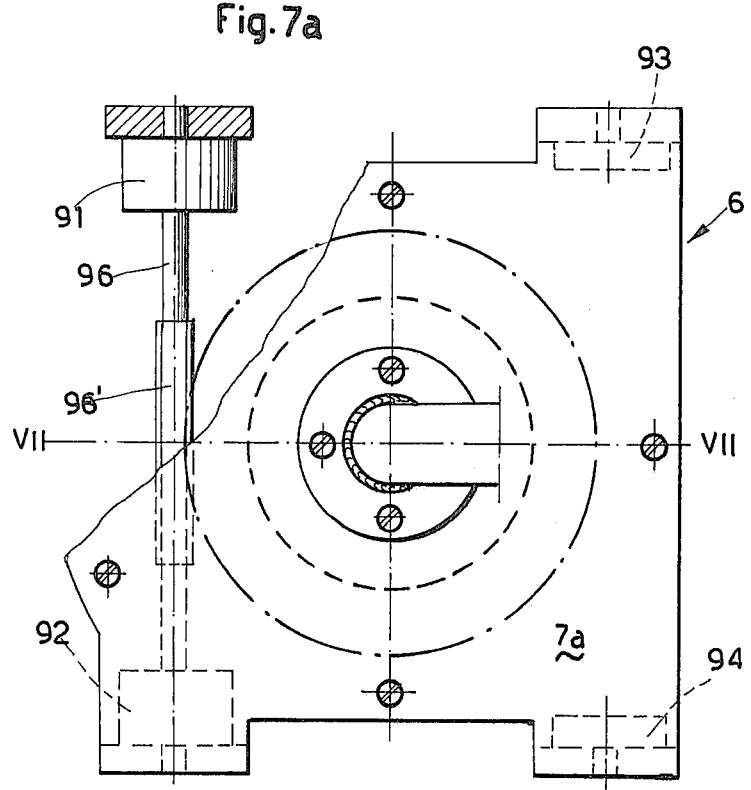
FIG. 7a is a top plan view of the third embodiment of the wheeled frame of the apparatus of this invention.

According to a third embodiment of this invention illustrated by FIGS. 7 and 7a, wheeled frame 6 is provided, the same as the preceding embodiment, with four wheels 91, 92, 93, 94 mounted in pairs on two parallel axles 96, 98 perpendicular to the symmetry plane of the frame. According to this embodiment, axle 96 on which wheels 91, 92 are keyed has a threaded portion 96' on the middle section thereof. Such threading engages the helical toothed periphery of a wheel 32a similar to wheel 32 of the first embodiment which wheel is similarly mounted on hub 95' of wall 95; an antifriction bearing 34a being inserted between wheel 32a and hub 95'. The same as with the first embodiment, the upper surface of wheel 32a is provided with a stop plate against which pin 38a comes to abut for limiting the travel of the wheeled frame.

Figure 8:
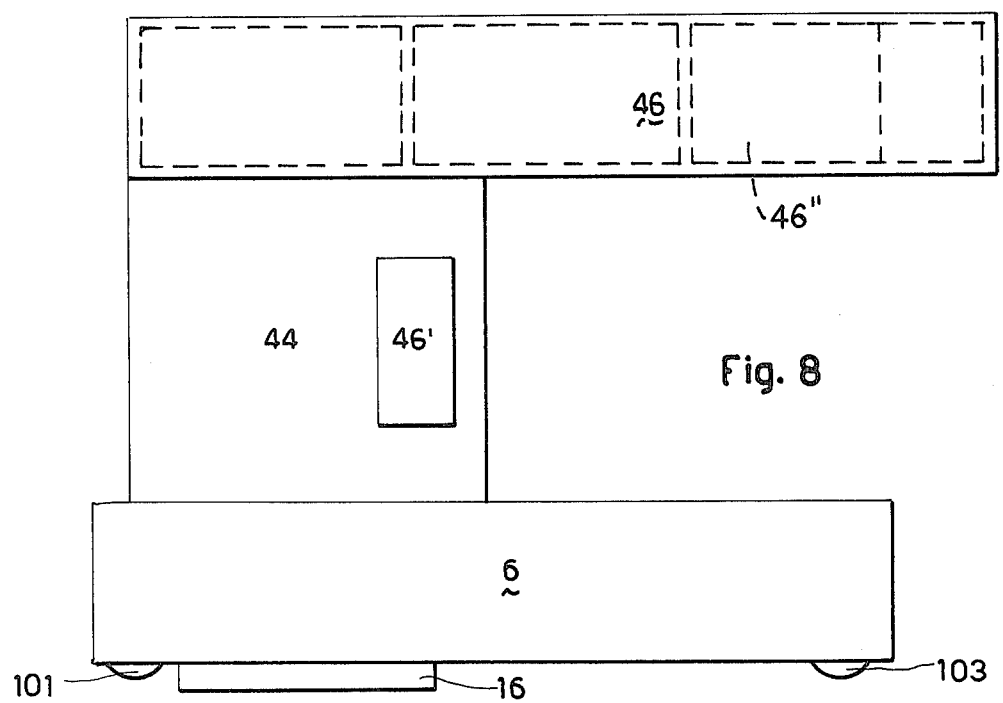
FIG. 8 is a schematic elevation view of the apparatus of this invention according to a fourth embodiment thereof.

According to a fourth embodiment of the invention illustrated by FIG. 8, the apparatus of this invention has a handy compact configuration which is particularly suited for smearing furniture items such as chairs, tables, benches, etc.

According to this embodiment, wheeled frame 6 has four wheels mounted in pairs on two parallel axles the same as with the second and third embodiment. The two pairs of wheels are indicated with 101, 103. From the frame bottom the lower portion of hollow disk 16 projects which carries the smear disk not shown in FIG. 8. Exhauster 44 is directly mounted on top of wheeled frame 6 and a handle 96 is mounted on top of the exhauster 44 in which handle the feeding batteries are housed. The air outlet from the exhauster is indicated by 46'. As shown by FIG. 8, handle 46 extends horizontally beyond the exhauster housing in the direction of the frame movement. For a better stability of the apparatus during the smearing operation, wheeled frame 6 is prolonged in the same direction as handle 46 and one pair of wheels 103 is located at the end of the prolonged portion of the frame. Because wheels 101 are closer to disk 16 than wheels 103, the former wheels are preferred for actuating any of the above described odometer means. In the following table the results are reported of radioactivity samples from surfaces of different kind by means of the apparatus of this invention.

The measured samples have been obtained by smearing a surface uniformly contaminated by radionuclide $Th^{228}$ with an activity of $1.10^{-5} \mu ci/cm^2$.

Four samples have been taken from each type of surface with the following results:

| Smeared surface: | Preaflex | Linoleum | Spoknol |
|---|---|---|---|
| | 385 c/s | 401 c/s | 446 c/s |
| | 371 | 423 | 429 |
| | 364 | 436 | 458 |
| | 367 | 407 | 471 |

The soundness of the apparatus and method of this invention has been proven by the above results in as much as the maximum changes of the measured radioactivity for the same kind of surface do not exceed 10% of the minimum values, which is deemed satisfactory for tests of this kind.

Four embodiments of this invention have been thus described. Obviously many changes and variations of them can be envisaged by those skilled in the art; however the inventors intend to cover all such changes and variants falling within the spirit and scope of the invention as expressed in the appended claims.

What we claim is:

1. An apparatus for the indirect monitoring of the radioactive comtamination of surfaces by smearing a predetermined area thereof by means of a thin disk of filter paper or similar material which apparatus comprises a hollow cylindrical member with parallel end walls and a peripheral wall which walls define a space within said member, one of said parallel walls being provided with an array of through bores; a pierced layer of elastic material over said pierced wall which layer is provided with a similar array of through holes as said pierced wall the holes of the latter and of the elastic layer being made to coincide, said thin disk of filter paper being applied over the exposed face of said elastic layer; a cylindrical guide attached to a wheeled frame in which guide said cylindrical member is slidably fitted, a helical spring being provided for biasing said member towards said surface, the space within said cylindrical member being connected to an exhausting means.

2. An apparatus as claimed in claim 1 wherein said pierced layer comprises a layer of elastomeric material of which the surface opposite to said pierced wall is rough.

3. An apparatus as claimed in claim 2 wherein said pierced layer is made of para rubber.

4. An apparatus as claimed in claim 1 which is provided with a tubular bar which terminates with a handle said exhauster means being inserted at a position along the bar and made to communicate with said space of the cylindrical member through said bar and through a swivel joint; batteries for feeding said exhauster means being housed in said handle.

5. An apparatus as claimed in claim 1 which further comprises four wheels for said wheeled frame two of said wheels being contained in the symmetry plane of the frame and the other two being located symmetrically with respect to said plane and rotatably mounted on axles perpendicular thereto.

6. An apparatus as claimed in claim 5 which further comprises an odometer means for measuring the distance travelled by said wheeled frame which odometer means comprises a pinion mounted on the axle of one of said wheels and a crown wheel rotatably mounted on a hub integral with said frame and a means for limiting the rotation of said crown wheel with respect to the frame.

7. An apparatus as claimed in claim 1 wherein said wheeled frame is provided with two pairs of wheels each pair being mounted on an axle parallel to the axle of the other pair and perpendicular to the symmetry plane of said wheeled frame which apparatus is provided with an odometer means comprising a screw shaft integral and coaxial with one of said axles which screw shaft engages a peripheral helical toothing of a wheel rotatably mounted on a hub of said frame.

8. An apparatus as claimed in claim 1 wherein said wheeled frame is provided with two pairs of wheels each pair being mounted on an axle parallel to the axle of the other pair and perpendicular to the symmetry plane of the frame which apparatus is provided with an odometer means comprising at least one screw shaft integral and coaxial with at least one of said axles which screw shaft engages a nut of which a side projection is slidable along a slot of the frame, an adjustable stop means being provided for limiting the travel of said projection along said slot.

9. An apparatus as claimed in claim 1 wherein said frame is supported on two pairs of wheels each pair being mounted on an axle parallel to the axle of the other pair and perpendicular to the symmetry plane of said wheeled frame; said exhauster is directly mounted on top of said frame; a handle is mounted on top of said exhauster which handle projects from the exhauster casing for the total of its length in the direction of movement of the wheeled frame, the latter being prolonged in the direction of the frame movement for providing a support for one wheel axle at a position under about half the length of the projecting handle.

* * * * *